United States Patent
Wolgen

(10) Patent No.: US 7,252,668 B2
(45) Date of Patent: Aug. 7, 2007

(54) DISTRACTION DEVICE FOR MAXILLOFACIAL SURGERY

(75) Inventor: Philippe Wolgen, Amsterdam (NL)

(73) Assignee: Faceworks Solutions & Technology Limited, Surrey (GB)

( * ) Notice: Subject to any disclaimer, the term of this patent is extended or adjusted under 35 U.S.C. 154(b) by 258 days.

(21) Appl. No.: 10/181,848

(22) PCT Filed: Jan. 17, 2001

(86) PCT No.: PCT/EP01/00567

§ 371 (c)(1),
(2), (4) Date: Sep. 23, 2002

(87) PCT Pub. No.: WO01/52755

PCT Pub. Date: Jul. 26, 2001

(65) Prior Publication Data

US 2003/0105463 A1    Jun. 5, 2003

(30) Foreign Application Priority Data

Jan. 17, 2000  (EP) ................................. 00200154

(51) Int. Cl.
*A61F 5/04* (2006.01)
(52) U.S. Cl. ..................................................... 606/53
(58) Field of Classification Search .................. 606/57, 606/58, 90, 105, 60, 68, 63, 69–71; 433/172, 433/174, 215; 604/229; 623/17.17, 17.18, 623/17.15
See application file for complete search history.

(56) References Cited

U.S. PATENT DOCUMENTS

| 5,769,850 | A |   | 6/1998 | Chin |
| 5,885,290 | A | * | 3/1999 | Guerrero et al. ............... 606/71 |
| 5,895,387 | A | * | 4/1999 | Guerrero et al. ............... 606/71 |
| 5,899,940 | A | * | 5/1999 | Carchidi et al. ............... 606/73 |
| 6,355,036 | B1 | * | 3/2002 | Nakajima .................... 606/57 |
| 6,383,189 | B1 | * | 5/2002 | Schumacher ................. 606/86 |

FOREIGN PATENT DOCUMENTS

| DE | 298 13 087 |   | 2/1999 |
| JP | 100432203 | * | 2/1998 |
| WO | WO 98/25538 |   | 6/1998 |

* cited by examiner

*Primary Examiner*—Eduardo C. Robert
*Assistant Examiner*—Michael J. Araj
(74) *Attorney, Agent, or Firm*—Greer, Burns & Crain, Ltd.

(57) ABSTRACT

The invention relates to a device that maybe used in maxillofacial surgery and dentistry. The device comprises a translating bracket with a cylinder and a fixed bracket with a chamber. A distraction screw is mounted through the cylinder and with one end resting on the chamber. By turning this screw when the device has been mounted on bone pieces osteogenesis can be achieved. The device can be made suitable for both dentulous and edentulous patients with alveolar defects.

14 Claims, 2 Drawing Sheets

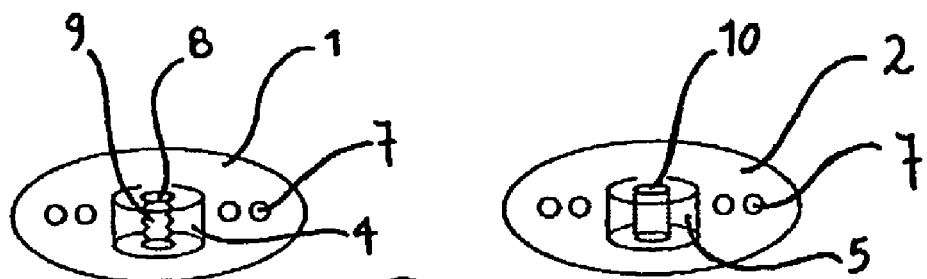
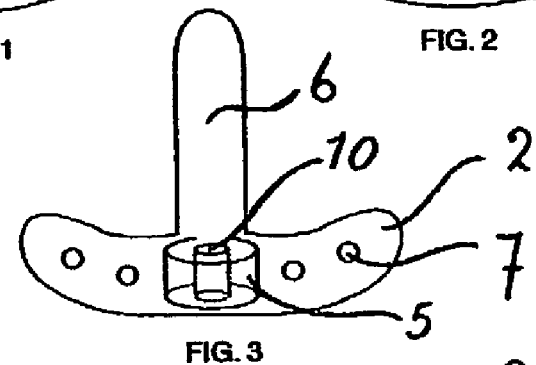
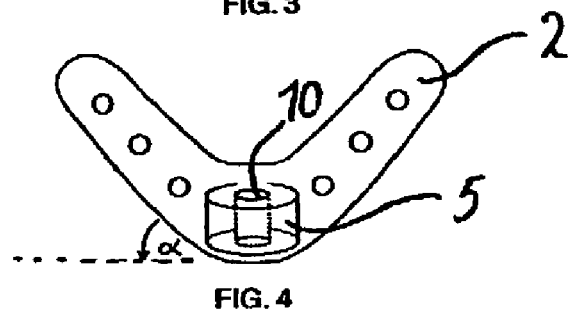
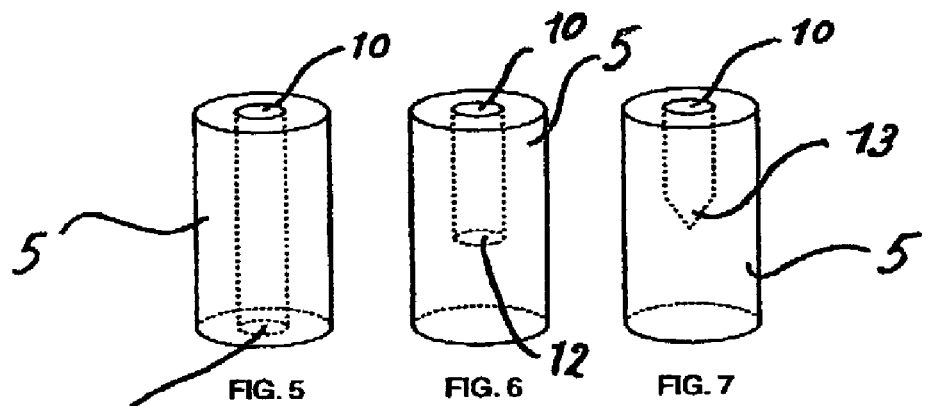
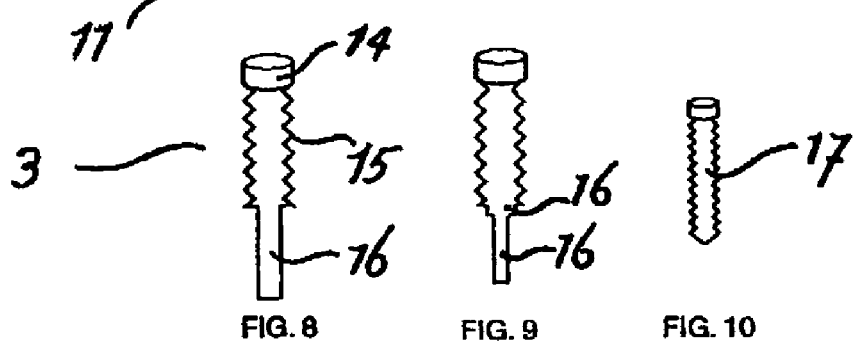

DISTRACTION DEVICE FOR MAXILLOFACIAL SURGERY

BACKGROUND OF THE INVENTION

Distraction Osteogenesis has been used in the facial skeleton following the principles laid down by Codvilla in 1905 and Ilizarov in 1952. McCarthy first introduced distraction osteogenesis in the mandible (lower jaw). Several distraction devices have been disclosed in the art.

McCarthy discloses in "Distraction of the craniofacial skeleton" (Springer Verlag, pages 68, 88, and 89; 1999) three extra-oral horizontal uniplanar and multiplanar distractors. The uniplanar distractors have two pin clamps, a distraction screw, and four percutaneous pins. The pins are of fixed length and about 80 mm long of which about 20 mm is fixed into the bone and 60 mm extends out of the bone. The diameter of the pin is between 10–15 mm in diameter. The distractor is placed percutaneously (through the skin of the face). The device is large, has a complex screw, and requires fixation through the skin with long pins. Therefore, fixation and removal needs to be performed under general anesthesia. McCarthy further describes two general drawings of intra-oral horizontal uniplanar distractors on page 98 and 99. On page 223, McCarthy discloses FIGS. 7.4 and 7.5 with two bulky intra-oral distractors with two guiding rails. FIG. 7.4 discloses a device with a distraction screw of about 3 cm long and a diameter larger than about 5 mm. The uniplanar distractor has two translating brackets, moving in opposite directions and no fixed bracket. All pieces are welded or soldered together. The device is large and complex and requires transmucosal fixation. FIG. 7.5 discloses a distraction screw of about 40 mm long and a diameter of about 6 mm The right fixed bracket is about 25 mm long, about 40 mm wide and about 8 mm thick. The left, translating bracket is about 40 m wide. The prominent interconnecting bars are positioned on top of the guiding rails. All pieces are welded or soldered together. The device is large and complex and requires transmucosal fixation Unidirectional distraction devices with the numbers 51-500-10, 51-500-15 and 51-500-20 by Martin, comprise each 2 guiding rails, a fixed bracket, a translating bracket, 1 distraction screw, 6 osteosynthesis pins and 1 or more cranks. The distractor requires an interconnecting bar between the guiding rails. This distractor is large and requires a complex surgical operation for fixation and removal under general anesthesia.

Dyna Form is marketed and is an intraoral distraction system for widening of the jaw. It consists of a translating bracket with a cylinder, a distraction screw, a fixed bracket that extends above the translating bracket, two guiding rails, and pins. The distraction screw pushes against the extension of the fixed bracket. Size and construction of the device make it too bulky to be used in vertical alveolar distraction.

Jaw lengthening distraction devices with numbers 51-525-06, 51-525-09, 51-525-12 and 51-525-15 by Martin, each comprises a fixed bracket with up to 14 perforations, a translating bracket with a cylinder and up to 10 perforations, and 1 chamber. The chamber is partially hollow and contains the entire length of a distraction screw, except for the head. The chamber contains the cylinder of the translating bracket. The use of many lateral pins could lead to damage to adjacent anatomical structures. The use of a lengthy and bulky chamber with cylinder may be uncomfortable during the period of distraction and are too large for use in vertical alveolar distraction. Further, it seems that the distraction screw cannot be replaced with an alternative distraction screw without removal of one or more of the brackets. Similar devices have been described in DE 297 16 635 and are marketed by Synthes.

A vertical alveolar distractor by Stryker Leibinger comprises a translating bracket, a fixed bracket, 10 to 20 perforations in total, and one distraction screw and was presented at a conference in Paris, in June 1999. One perforation in the translating bracket is used as a cylinder for the distraction screw. The brackets are relatively thick. Some of the perforations are positioned in the distraction gap and interfere with the neo-osteogenic site. The use of many lateral pins could lead to damage to adjacent anatomical structures.

U.S. Pat. No. 5,769,850 (Chin) describes a device for vertical alveolar distraction osteogenesis containing a translating upper bracket with a cylinder, a fixed bracket with a chamber, a distraction screw, and pins. The distraction screw has one or more sharp ends. It is required to drill a hole in the bone to allow for rotation of the screw end within the 3 osseous segments. The device has sharp edges, does not have a smooth surface and extends into the osteogenesis site. The pins are screwed through the bracket towards the distraction screw. The device does not have a guiding rail and has a chamber, which is short in length. Similar devices are sold under the Lead System trademark name.

JP 10043203 (Keisei Ika) describes 2 types of devices: one device with a connection between the jaw and the cranium for extending the jaw away from the cranium and another device with two connections to the jaw for lengthening the ascending ramus of the mandible (=lower jaw). The devices contain a translating bracket (plate) with a cylinder, a fixed bracket with a chamber with an aperture (hole), and a distraction screw. The device extends (distracts) the ascending ramus of the mandible away from the cranium, uses pins and has a thin chamber. Devices use extensions into the site of osteogenesis. The devices have sharp edges, particularly the end of the screw and the brackets, and do not have a smooth surface. The prominent and sharp edges of the plate face away from the underlying jaw bone towards and into the soft tissues. Devices have extensions into the site of osteogenesis. None of the devices has a guiding rail. Devices are large with sizes of up to 100 mm and more, which is too large to be used for vertical alveolar distraction. Further, the pins are not threaded.

U.S. Pat. No. 5,895,387 (Guerrero) describes a distraction device for lengthening the jaw and for extending the cranium. The device has a translating bracket with a cylinder, a fixed bracket, and pins. However, the device has a large size and is not described for vertical alveolar distraction. Guerrero uses an anvil area and does not have an aperture in the chamber. The device does not have a guiding rail. The device has sharp edges instead of a smooth surface. In fact, it has "clamps" that extend into the site of osteogenesis.

U.S. Pat. No. 5,980,252 (Samchukov) describes a tooth borne alveolar distraction device containing a translating bracket with cylinder, a distraction screw, and a fixed bracket. The device does not have pins and does not have a guiding rail. The device has sharp edges and extensions into the site of osteogenesis. The distraction screw does not push against the chamber and the screw cannot easily be replaced during the distraction.

DE 298 13 087 (Karl Leibinger) describes a distraction device containing a translating bracket with a cylinder, a distraction screw, a fixed bracket and pins. The device has 2 guiding rails on the side of the screw to add to the stability while extending the length of the jaw. However, the fixed bracket does not have an aperture and the device seems too bulky for vertical alveolar distraction.

Surprisingly, we have found that one or more problems of the distractors of the prior art can be overcome by using the distractor device of the present invention.

BRIEF SUMMARY OF THE INVENTION

The invention relates to a device comprising two or more brackets, and a distraction screw. Preferably, the device comprises lateral pins. Optionally, the device comprises one or more guiding rails. Optionally, the device comprises an interconnecting bar connected with another device.

The invention preferably relates to a vertical alveolar osteogenic microdistractor device comprising a translating bracket with a cylinder, a fixed bracket with a chamber with an aperture, a distraction screw, and lateral pins characterized in that the device does not interfere with the osteogenic side. Preferably, the invention relates to a device, wherein the device is smooth and without sharp edges. Preferably, the invention relates to a device wherein the brackets do not have extensions that are directed perpendicularly to the distraction screw and perpendicularly to the brackets, at a level between the brackets and directed away from the distraction screw into the site of osteogenesis. Preferably, the invention relates to a device wherein the device comprises a guiding rail and/or an interconnecting bar. Preferably, the invention relates to a device wherein the distraction screw is replaceable.

A preferred embodiment of the invention is a distractor composed of four parts, including two brackets, the vertical screw, four titanium lateral (osteosynthetic) pins. The present invention further relates to a device comprising a translating bracket. with a cylinder, a fixed bracket with a chamber with an aperture, a distraction screw, and lateral pins for use in vertical alveolar osteogenesis. The present invention further relates to a method of manufacturing a device comprising a translating bracket with a cylinder, a fixed bracket, a guiding rail, and a distraction screw, wherein the guiding rail slides through the translating bracket, and wherein the distraction screw is turned through the cylinder and placed into the aperture of the chamber of the fixed bracket.

The present invention further relates to a method of vertical alveolar distraction of two bone pieces using a device comprising a translating bracket with a cylinder, a fixed bracket with a chamber with an aperture, and a distraction screw wherein the fixed bracket is connected to one piece of bone, the translating bracket is connected to the other piece of bone, the distraction screw is inserted through the cylinder of the translating bracket and placed in the aperture of the chamber of the fixed bracket, wherein the two pieces of bone are distracted by turning the distraction screw, and wherein the device does not interfere with the neo-osteogenic site.

The present invention further relates to a fixed bracket comprising a chamber and perforations and to the manufacture thereof The present invention further relates to a translating bracket comprising a cylinder and perforations and to the manufacture thereof.

Further Advantages

The dimensions of the device are suitable and tailored to distraction histio-osteogenesis in the resorbed and atrophied orofacial osseous skeleton. With the design of the device an attempt is made to provide for all parameters affecting distraction osteogenesis, for instance in patients with the edentulous mandible and/or maxilla jaws, and dentulous (tooth bearing) patients with alveolar defects. The simplicity and the size of the device make it easily applicable and more suited in the oral cavity and in the orofacial skeleton.

The device of the present invention has further advantages over the prior art. The device is small without any internal empty space (this may be called an "open structure"). Its small size allows for implantation underneath the mucosa, under the mucoperiosteal layer. The small size further leaves little scar tissue after distraction.

The design of the device allows for placement and removal through a simple surgical procedure, without the requirement for general anesthesia of the patient. The size and design of the device presented enables the surgeon to use a minimally invasive surgical approach when placing the device. The design avoids interference with the site of neo-osteogenesis. The device is further designed such that it produces little or no inconvenience or irritation for the patient during the period of distraction. Furthermore, a preferred embodiment of the device of the invention allows for changing the distraction screw without removal of the brackets. The design of the device makes the chance of infections and other complications particularly small. As a consequence of the design, the device has high rigidity, potentially leading to fewer complications than the devices of the prior art. The design avoids micro movements at the site of neo-osteogenesis.

The design of the device accommodates for the specific features of the tight mucoperiosteal layer. In order to protect this mucoperiosteal layer under which the device is to be inserted:

(i) the edges of the brackets are preferably rounded/curved;
(ii) the transition from chamber to bracket and from cylinder to bracket is preferably smooth and rounded off,
(iii) the proposed titanium or any material used is preferably highly polished in order to avoid bacterial accumulation/ bacterial vegetation at the surface of the material; and
(iv) the top part of the guiding rail and the edges of the interconnecting bar are rounded off.

BRIEF DESCRIPTION OF THE DRAWINGS

FIG. 1 is a front view of a translating bracket having a cylinder in accordance with the present distraction device;

FIG. 2 is a front view of a fixed bracket having a chamber in accordance with the present distraction device;

FIG. 3 is a front view of a fixed bracket having a chamber and a guide rail in accordance with the present distraction device;

FIG. 4 is a front view of a fixed bracket having a chamber where the fixed bracket is oriented at an angle;

FIG. 5 is a front view of a first embodiment of a chamber of the fixed bracket in accordance with the present distraction device;

FIG. 6 is a front view of a second embodiment of a chamber of the fixed bracket in accordance with the present distraction device;

FIG. 7 is a front view of a third embodiment of a chamber of the present fixed bracket;

FIG. 8 is a front view of a distraction screw having a head, a threaded shaft and a non-threaded tip;

FIG. 9 is a front view of a distraction screw having two indentations;

FIG. 10 is a front view of an osteosynthetic pin;

DETAILED DESCRIPTION OF THE PREFERRED EMBODIMENT

Figure 11:
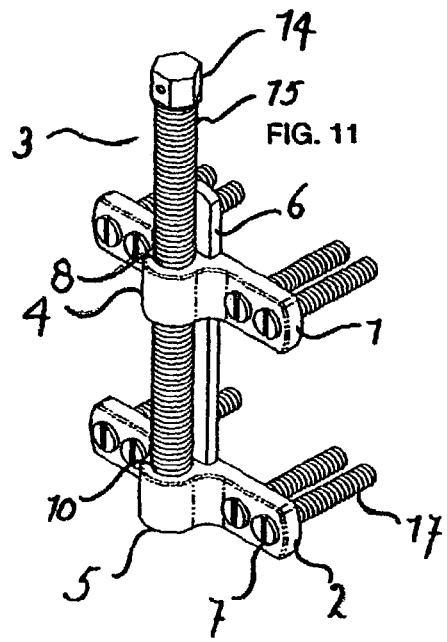
FIG. 11 is an assembled perspective view of the present distraction device having a guide rail.
Figure 12:
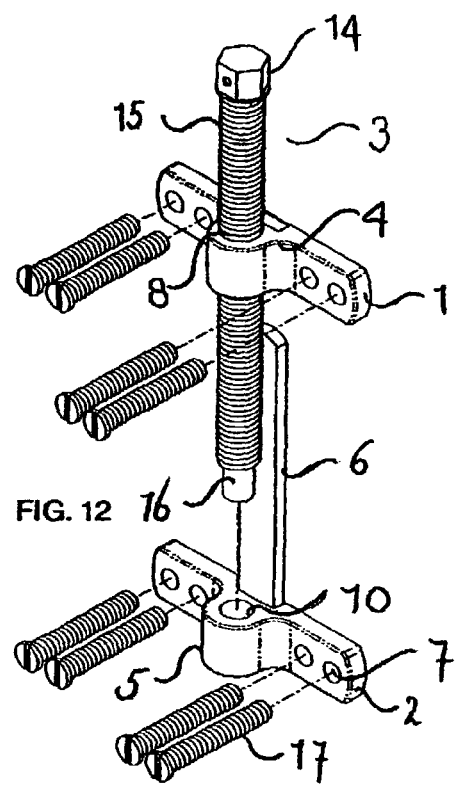
FIG. 12 is a partially exploded perspective view of the distraction device shown in FIG. 11.
Figure 13:
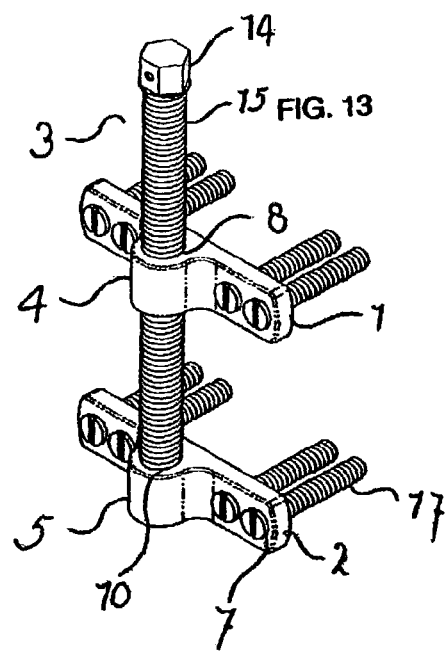
FIG. 13 is an assembled perspective view of the present distraction device lacking a guide rail.
Figure 14:
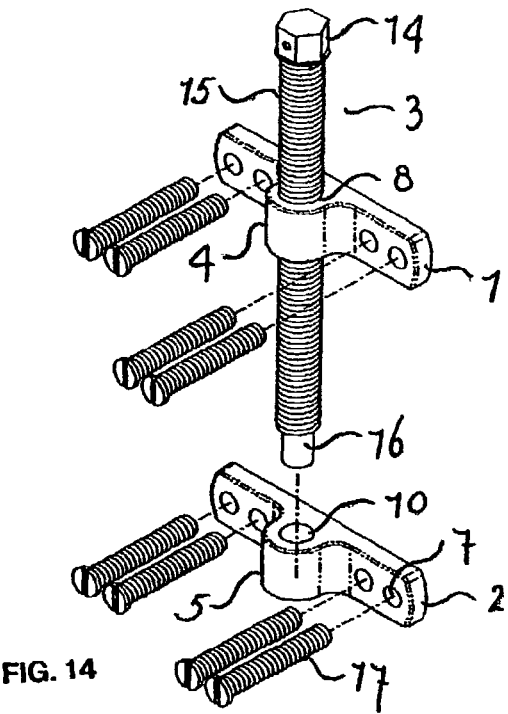
FIG. 14 is a partially exploded perspective view of the distraction device shown in FIG. 13.

The device of the invention is preferably used as a maxillofacial distractor, an osteogenic device, or a bone conducing device for the alveolar bone. Before use, the device is preferably sterilized (or autoclaved).

The device of the invention preferably comprises at least 2 brackets, for instance up to 3. More preferably, the device contains 2 brackets. Preferably, one of the brackets is a translating, cranial (upper) bracket and the other a fixed, caudal (lower) bracket. For the purpose of this invention, 'translating' is defined as being able to move up and down relative to the distraction screw (viewed in the vertical plane). For the purpose of this invention, 'fixed bracket' is defined as a bracket that is not moving up and down relative to the distraction screw during distraction. Preferably, the distraction screw can be turned relative to the fixed bracket.

Preferably, the brackets, the distraction screw, the lateral pins and the guiding rails (if present) and the interconnecting bars (if present) are made of biocompatible materials, such as metals, polymers, and mixtures thereof. Preferred examples are metals (steel, Titanium), metal alloys (Nickel-Titaniun, Cobalt-Chromium alloys, Cobalt-Chromium-Nickel, CrCoMo), and polylactides. The most preferred example is Titanium. Titanium has extraordinary tissue compatibility. In order to improve the rigidity of the device, each of the brackets is preferably made of one piece of material. Preferably, the material and edges of the entire device are smooth without sharp edges.

The device preferably has a length of smaller than 35 mm, more preferably smaller than 30 mm, most preferably smaller than 25 mm, for instance 20 mm, and preferably larger than 3 mm, more preferably larger than 5 mm, most preferably larger than 8 mm, for instance 10 mm The device preferably has a width smaller than 35 mm, more preferably smaller than 30 mm, most preferably smaller than 25 mm, and preferably larger than 1 mm, more preferably larger than 2 mm, most preferably larger than 3 mm. The device preferably has a thickness smaller than 35 mm, more preferably smaller than 30 mm, and preferably larger than 1 mm, more preferably larger than 2 mm, most preferably larger than 3 mm, for instance between 5 and 10 mm.

Translating Bracket

The translating bracket preferably comprises a cylinder. Preferably, the cylinder is hollow. Preferably, the cylinder is internally threaded. Preferably, the cylinder is located centrally (viewed in the sagittal or- transversal plane) of and anteriorly (viewed in the sagittal or transversal plane) to the translating bracket. Preferably, the length of the cylinder runs perpendicularly to the plane of the bracket and perpendicularly to the plane of the distraction screw.

The inner diameter of the cylinder is preferably from 0.5 mm, more preferably from 1 mm, most preferably from 1.5 mm and preferably up to 7 mm, more preferably up to 6 mm, most preferably up to 5 mm, in particularly preferably smaller than 4 mm, for example 2 mm. The height of the cylinder is preferably from 0.2 mm, more preferably from 0.4 mm, most preferably from 0.6 mm, particularly larger than 0.8 mm and preferably up to 10 mm, more preferably up to 8 mm, most preferably up to 6 mm, for example 2.5 mm The width of the cylinder is preferably from 1 mm, more preferably from 2 mm, most preferably from 3 mm, preferably up to 25 mm, more preferably up to 20 mm, most preferably up to 15 mm, for example between 5 and 10. The thickness of the cylinder is preferably smaller than 25 mm, more preferably smaller than 20 mm, most preferably smaller than 15 mm and preferably from 1 mm, more preferably from 2 mm, most preferably from 3 mm, for instance between 5 and 10 mm.

The translating bracket may not comprise a perforation. However, it is preferred that the translating bracket comprises one or more perforations. The perforations can be used for fixating the translating bracket with lateral pins to the underlying alveolar (jaw) bone that is to be distracted (moved away from the underlying bone). Preferably, the perforations are positioned in the horizontal (transversal) plane of the translating bracket, and are preferably completely embedded in the bracket. Preferably, the lateral perforations are located perpendicular to the cylinder and perpendicular to the distraction screw and directed away from the distraction screw in a sagittal or transversal plane. Preferably, the perforations are round. The perforations are preferably smooth and not internally threaded. The perforations match the diameter of the lateral pins and preferably have a diameter of from 0.2 mm, more preferably from 0.4 mm, most preferably from 0.6 mm, preferably up to 5 mm, more preferably up to 4 mm, for instance 0.9 mm. The number of perforations of the translating bracket to be used depends on the forces that are exercised on the device during distraction, while, at the same time, damage to the nearby anatomical structures has to be avoided. Preferably, the translating bracket contains at least one perforation, for instance up to 10, preferably up to 8, more preferably up to 6, most preferably up to 4, in particular up to 3, for example two or one perforation. The perforations may be located on either side of (lateral to, viewed in a transversal or sagittal plane) the cylinder (if present), on one side of the cylinder, superior or inferior to or posterior to the cylinder. Preferably, the thickness of the bracket around the perforation is at least 0.1 mm, more preferably at least 0.2 mm.

In a particular embodiment of the invention, the perforations are placed in a line at an angle relative to the distraction screw. This embodiment can be used in regions where more retention for the brackets is required. For instance, in the intermental region, the perforations should be multiple on either side and preferably under an angle relative to the distraction screw in order to counteract the lingual tension forces of the musculature on the inside of the mouth. Preferably, the angle is between 90 and 0 degrees, more preferably between 30 and 60 degrees, for instance at 45 degrees.

The length of the translating bracket is preferably from 0.5 mm, more preferably from 1 mm, most preferably from 2 mm and preferably to 30 mm, more preferably to 20 mm, most preferably to 15 mm, in particular up to 10 mm, for instance 3 mm. The translating bracket preferably has a width of from 2 mm, more preferably from 3 mm, most preferably from 4 mm, and preferably to 25 mm, more preferably to 20 mm, most preferably to 18 mm, in particular to 15 mm, for instance from 5 mm to 10 mm. The thickness (including the cylinder) is preferably larger than 1 mm, more preferably larger than 2 mm, most preferably larger than 2 mm, and in particular larger than 3 mm, and preferably up to 25 mm, more preferably up to 20 mm, most preferably up to 15 mm, for instance from 5 mm to 10 mm.

Fixed Bracket

Preferably, the fixed bracket comprises one or more (2, 3 or 4) chambers. More preferably, the device comprises one chamber. One or more of the chambers may-be solid. Preferably, one chamber comprises an aperture. The aperture can be in the shape of a cavity. Preferably, the aperture is a hollow tube. More preferably the aperture is a cylinder. Preferably, the chamber is in the shape of a cylinder. This facilitates easy surgical fixation and removal of the device and allows for exchange, of the distraction screw during activation of the device.

The aperture in the chamber may have different widths at different distances from the chamber surface. For instance, the aperture in the chamber may be wider (indentation) or narrower (extension) inside the chamber as compared to the opening in the surface of the chamber.

Preferably, the diameter of cylindrical aperture in the chamber is from 0.5 mm, more preferably from 1 mm, most preferably from 1.5 mm, preferably up to 7 mm, more preferably up to 6 mm, most preferably up to 5 mm, in particularly preferably smaller than 4 mm, for instance 2 mm. Preferably, the length of the cylindrically shaped aperture is larger than 0.2 mm, more preferably larger than 0.5 mm, most preferably larger than 0.8 mm and preferably smaller than 25 mm, more preferably smaller than 20 mm, most preferably smaller than 15 mm, for instance 2 or 3 mm.

In a preferred embodiment of the invention, the chamber has an aperture at the top. The bottom of the aperture may be open (i.e. the chamber is perforated) or it may be solid (i.e. the chamber is not perforated). The aperture allows the distraction screw to be inserted and turned freely. If present, the bottom of the aperture could be flat, but is preferably V-shaped. The inner surface of the chamber is smooth and not threaded. In this embodiment, the aperture is preferably cylindrically shaped.

The length of the chamber is preferably larger than 0.2 mm, more preferably larger than 0.4 mm, most preferably larger than 0.6 mm, particularly larger than 0.8 mm and preferably up to 20 mm, more preferably to 10 mm, most preferably to 8 mm, for instance 2.5 mm. The width of the chamber is preferably from 1 mm, more preferably from 2 mm, most preferably from 3 mm, preferably up to 25 mm, more preferably up to 20 mm, most preferably up to 15 mm, for example between 5 and 10. The chamber preferably has a thickness smaller than 25 mm, more preferably smaller than 20 mm, most preferably smaller than 15 mm and preferably from 1 mm, more preferably from 2 mm, most preferably from 3 mm, for instance between 5 and 10 mm.

The fixed bracket may not comprise a perforation. However, it is preferred that the fixed bracket comprises one or more perforations. The perforations can be used for fixating the fixed bracket to the underlying alveolar (jaw) bone with lateral pins. Preferably, the perforations are positioned in the horizontal (sagittally or transversally in the fixed bracket) plane of the fixed bracket, and are preferably completely embedded in the brackets. Preferably, the perforations are round. The perforations are preferably smooth and not internally threaded. The perforations match the diameter of the lateral pins and preferably have a diameter of from 0.2 mm, more preferably from 0.4 mm, most preferably from 0.6 mm, preferably up to 5 mm, more preferably up to 4 mm, for instance 0.9 mm. The number of perforations of the fixed bracket to be used depends on the forces that are exerted on the device during distraction, while, at the same time, damage to the nearby anatomical structures needs to be avoided. Preferably, the fixed bracket contains at least one perforation, for instance up to 10, preferably up to 8, more preferably up to 6, most preferably up to 4, in particular up to 3, for example 2 or one perforation. The perforations may be located on either side of the chamber (if present), on one side of the chamber, or posterior to the chamber. Preferably, the thickness of the bracket around the perforation is at least 0.1 mm, more preferably at least 0.2 mm.

In a particular embodiment of the invention, the perforations are placed in a line at an angle relative to the distraction screw, in a sagittal or transversal plane relative to the distraction screw. This embodiment can be used in regions where more retention for the brackets is required. For instance, in the intermental region, the perforations should be multiple on either side and preferably under an angle relative to the distraction screw in order to counteract the lingual tension forces of the musculature on the inside of the mouth. Preferably, the angle is between 90 and 0 degrees, more preferably between 30 and 60 degrees, for instance at 45 degrees.

The length of the fixed bracket is preferably from 0.5 mm, more preferably from 1 mm, most preferably from 2 mm and preferably to 30 mm, more preferably to 20 mm, most preferably to 15 mm, in particular up to 10 mm, for instance 3 mm. The fixed bracket preferably has a width of from 2 mm, more preferably from 3 mm, most preferably from 4 mm, in particular from 25 mm, and preferably to 20 mm, more preferably to 18 mm, particularly preferred to 15 mm, for instance 10 mm. The thickness (including the chamber) is preferably larger than 1 mm, more preferably larger than 2 mm, most preferably larger than 3 mm, and preferably up to 25 mm, more preferably up to 20 mm, most preferably up to 15 mm, for instance from 5 mm up to 10 mm.

Distraction Screw

Preferably, the device of the present invention comprises one or more distraction screws. More preferably, the device comprises one distraction screw. Preferably, the distraction screw comprises a head, a shaft and a tip.

The length of the distraction screw may vary depending on the required distraction. Preferably, the length of the screw is up to 35 mm, more preferably up to 30 mm, most preferably up to 25 mm, for instance 20 mm, and preferably larger than 3 mm, more preferably larger than 5 mm, most preferably larger than 8 mm, for instance 10 mm.

Preferably, the head of the distraction screw has a groove (one groove or an "astrix" insertion). Preferably, the groove covers the entire diameter of the head. The circumference of the head is preferably hexagonally shaped, more preferably in all planes. In order to enable the surgeon or patient to easily read the distance of distraction after having turned the distraction screw, the head of the distraction screw is preferably marked on the surface between the center and the side of the screw. The mark may be an indentation in the screw and/or may consist of a different color.

Preferably the shaft of the distraction screw is threaded. Preferably, the pitch of the thread is larger than 0.1 mm, more preferably larger than 0.15 mm, most preferably larger than 0.2 mm, and preferably smaller than 4 mm, more preferably smaller than 3 mm, most preferably smaller than 2.5 mm Examples of a pitch are 0.25 mm, 0.3 mm, 0.5 mm, 1 mm, 1.5 mm and 2 mm. Preferably, the diameter of the shaft is smaller than 7 mm, more preferably smaller than 6 mm, most preferably smaller than 5 mm, in particularly preferably smaller than 4 mm, preferably larger than 0.5 mm more preferably larger than 1 mm, most preferably larger than 1.5 mm, for instance 2 mm.

Preferably, the distraction screw is straight. Preferably, the shaft has one or more extensions and/or indentations, most preferably one indentation. The extensions or indentations may be circular and/or lateral. They preferably have a smooth surface. Preferably, the extension or indentation extends along the length of the distraction screw to the tip. The diameter of extensions may be at least 0.5 mm larger than the diameter of the shaft, more preferably at least 1 mm, most preferably at least 2 mm, and preferably at most 20 mm, more preferably at most 16 mm. The diameter of indentations may be at least 0.1 mm smaller than the diameter of the shaft, more preferably at least 0.2 mm, and preferably at most 3 mm, more preferably at most 2 mm. Preferably, the length of the extension and/or indentation matches the chamber of the fixed bracket and is preferably larger than 0.2 mm, more preferably larger than 0.5 mm, most preferably larger than 0.8 mm and preferably smaller than 25 mm, more preferably smaller than 20 mm, most preferably smaller than 15 mm, for instance 2 or 3 mm. Preferably, the diameter of extensions and/or indentations matches the aperture in the chamber and is preferably from 0.5 mm, more preferably from 1 mm, most preferably from 1.5 mm, preferably up to 7 mm, more preferably up to 6 mm, most preferably up to 5 mm, in particularly preferably smaller than 4 mm, for instance 2 mm.

The tip of the distraction screw may be flat, spherical or V-shaped. If V-shaped, the distraction screw may have a smooth and polished tip.

Lateral Pin

The brackets can be glued on or adhered to the underlying anatomic structures. However, to be able to withstand larger forces, the brackets are preferably connected through lateral pins. Preferably, the pins are threaded. The pins may vary in length depending on the thickness of the underlying alveolar (jaw) bone, but are preferably from 2 mm, more preferably 3 mm, most preferably 4 mm, preferably up to 20 mm, more preferably 10 mm, most preferably up to 8 mm, particularly up to 6 mm in length The diameter of the pins-is preferably from 0.2 mm, more preferably from 0.4 mm, most preferably from 0.6 mm, preferably up to 5 mm, more preferably up to 4 mm, for instance 0.9 mm.

Preferably, the head of the lateral pin has a groove. Preferably, the groove covers the entire diameter of the head.

Preferably, the pitch of the threads of the lateral pins is larger than 0.1 mm, more preferably larger than 0.15 mm, most preferably larger than 0.2 mm, and preferably smaller than 4 mm, more preferably smaller than 3 mm, most preferably smaller than 2.5 mm. Examples of a pitch are 0.25 mm, 0.3 mm, 0.5 mm, 1 mm, 1.5 mm and 2 mm.

The pins have a tip for screwing into the bone. This is the only part of the device that has a sharp edge. However, this tip is not exposed to the soft tissue of the mouth. Therefore, devices of the present invention preferably contain no sharp edges that are in contact with the mouth. Preferably, the only sharp element of the device of the invention is the tip of the lateral pins.

Guiding Rail

Optionally, one or more of the brackets comprise one or more guiding rails. If present, the guiding rail is preferably connected to the fixed bracket. If present, the guiding rail can be attached to the bracket but is preferably continuous with the bracket, i.e. the bracket and the guiding rail are made from one piece of material. Preferably, the guiding rail has a smooth and polished surface.

If present, the guiding rail is preferably connected at the posterior (back) part of the bracket, although the guiding rail(s) may also be connected elsewhere.

In order to prevent the guiding rail from sticking out and damaging the anatomical structures in the mouth, the guiding rail is preferably shorter than the distraction screw. Preferably, the guiding rails has a length of smaller than 35 mm, more preferably smaller than 30 mm, most preferably smaller than 25 mm and preferably up from 3 mm, more preferably up from 5 mm, most preferably up from 8 mm, for instance from 15 to 20 mm.

Preferably the guiding rail has a width of from 0.1 mm, more preferably from 0.5 mm and preferably up to 6 mm, more preferably up to 5 mm, most preferably up to 4 mm, for instance 3 mm. Preferably the guiding rail has a thickness of from 0.1 mm, more preferably 0.5 mm and preferably up to 3 mm, more preferably up to 2 mm, most preferably up to 1.5 mm for instance 1 mm.

If 2 or more guiding rails are present, then the guiding rails are preferably not connected with a bar. Such a device would increase the size of the distractor and potentially lead to complications.

Interconnecting Bar

In certain cases, two or more distractors may be indicated, for instance to move larger osteotomized (cut) bone. The use of bigger distractors would increase the chance of infections. Also, bigger distractors are less likely to be tolerated by the patient. To assure parallel movement of the two or more pieces of alveolar bone, an interconnecting bar between two brackets may be used. A gradual distraction over a long trajectory with two or more distractors is preferred over distraction with a single large distractor.

Therefore, an embodiment of the present invention relates to 2 or more (up to 3, preferably 2) devices with one or more (up to 2; preferably 1) of the brackets connected to the brackets of another distractor by way of one or more (preferably 1) interconnecting bars. Preferably, a guiding rail is used for this embodiment of the invention. The lateral perforations through each of the brackets may be situated within the interconnecting bar.

Positioning of the Parts of the Distractor

Preferably the device comprises brackets, and a distraction screw. Preferably, the distraction screw runs perpendicularly through the cylinder on the translating bracket. Preferably, the screw can turn in the thread of the cylinder of the translating bracket. Preferably, the distraction screw rests on and slots into (preferably a smooth area of) the fixed bracket after placement by the surgeon. By turning the distraction screw, the screw will push against the fixed bracket and move the translating bracket along the thread of the distraction screw.

In order to reduce the size of the device and improve the stability, the chamber of the fixed bracket is preferably located entirely on one side (for instance below) of the cylinder of the translating bracket (in the vertical plane relative to the cylinder). Preferably, the cylinder of the translating bracket is located (viewed in the vertical and/or sagittal view) entirely outside (and preferably on one side) of the chamber of the fixed bracket. The chamber of the fixed bracket and the rest of the fixed bracket (that comprises at least part of any perforations) are preferably located on the same side (viewed in a sagittal or transversal plane) of the translating bracket. Thus, the chamber of the fixed bracket does not extend to the other side of the cylinder of the translating bracket.

Preferably, the distraction screw rests on the surface of the fixed bracket. Preferably, the distraction screw slots into the aperture of the fixed bracket with an extension and/or an indentation. Preferably, the distraction screw rests against the surface of the fixed bracket on the side facing the translating bracket. Preferably, this surface is part of the chamber of the fixed bracket. The surface can, for instance, be the outer surface of the chamber on fixed bracket and/or the bottom of the aperture in the chamber. Preferably, the bottom of the aperture, if present, matches the shape of the tip of the distraction screw.

As indicated above, the shaft of the distraction screw may optionally have one or more extensions (for instance circular and lateral) and/or one or more indentations (for instance circular and lateral). These may be positioned at one or more locations towards and/or at the tip of the distraction screw.

The distraction screw is preferably positioned in the aperture of the fixed bracket. Lateral extensions and or indentations of the distraction screw may rest against the surface of the fixed bracket. Extensions and/or indentations of the distraction screw may also be positioned inside the fixed bracket and match with indentations and/or extensions of the aperture of the fixed bracket. Such extensions and indentations may prevent the distraction screw from moving out or through (up and down; in the vertical plane) the fixed bracket. Use of these extensions or indentations may stabilize the distraction screw relative to the fixed bracket and make the connection between the fixed bracket and the distraction screw tighter (rigid/robust).

In a preferred embodiment of the invention, the chamber of the fixed bracket has an aperture on the surface at the side facing the translating bracket. The aperture extends into the chamber. The bottom of the aperture is solid and not perforated on the other side of the chamber. The distraction screw is inserted and turned freely in the aperture of the fixed bracket. Preferably, the distraction screw rests on the bottom of the aperture and/or on the outer surface of the fixed bracket (for instance through a lateral extension that might be circular, as discussed above). The distraction screw can be inserted in the fixed bracket, for instance for a distance from 0.5 mm to 3 mm, may stabilize the distraction screw relative to the fixed bracket and make the connection between the fixed bracket and the distraction screw tighter (rigid/robust).

In an especially preferred embodiment of the invention, the distraction screw does not have extensions inside in the aperture of the chamber of the fixed bracket. This allows the distraction screw to be removed from the fixed bracket through the aperture at the top and from the translating bracket. This preferred embodiment allows the surgeon to replace the distraction screw, for instance with a longer distraction screw, during the process of distraction and without unscrewing the brackets from the underlying bone.

Preferably, the device of the invention does not interfere with the site of osteogenesis. It is therefore preferred that the brackets do not have extensions that are directed perpendicularly to the distraction screw and/or perpendicularly to the brackets, at a level between the brackets and directed away from the distraction screw into the site of osteogenesis (viewed in a sagittal or transversal plane). Preferably, the distraction screw is not present in the site of osteogenesis. Preferably, the lateral pins are located perpendicularly to the distraction screw and preferably perpendicularly to the brackets and preferably directed away (sagitally or transversally) from the distraction screw into the bone. To improve the healing process, the lateral pins do preferably not interfere with the site of neo-osteogenesis and preferably do not damage the surrounding anatomical structures. Preferably, perforations (preferably embedded) on the fixed bracket and/or on the translating bracket face away from the distraction screw viewed in a vertical (sagittal or transversal) plane.

The optional guiding rail slides through the opposing bracket. For instance, if connected to the fixed bracket, it slides through the translating bracket, or visa versa. The rail guides the brackets in the right direction and makes the connection tighter (rigid/robust).

If present, the guiding rail is most preferably connected at the posterior (back) part of the bracket, posterior to the distraction screw and parallel to the distraction screw. However, the guiding rail(s) may also be connected elsewhere, for instance around the distraction screw. The guiding rail may also be placed parallel and adjacent, for instance on the sides or in the front of the distraction screw (when viewed in a sagittal or transversal plane). If placed in the front (anteriorly), the guiding rail will also protect the anatomical structures from being exposed to the distraction screw.

The Lateral Pins may vary in length and may be used either for monocortical or bicortical fixation.

Manufacture of the Device

The device of the present invention is preferably manufactured by preparing the translating bracket with a cylinder, the fixed bracket and the distraction screw, and turning the distraction screw through the cylinder of the translating bracket. Preferably, the device comprises lateral pins.

Preferably the parts of the device of the present invention are manufactured without using welding or soldered connections. Instead each part is preferably manufactured out of one solid piece through casting. Therefore, preferably the distraction screw is manufactured out of one piece, preferably the translating bracket is manufactured out of one piece, and preferably the fixed bracket is manufactured out of one piece.

Distraction Process

In edentulous patients (those who have no dentition) 3-dimensional resorption and atrophy has affected both the mandible (lower jaw), maxilla (upper jaw) and the soft tissues of the face. The cortical (outer) surface of the mandible is in those patients (classified as Cawood IV, V and VI) mostly remodeled to a convex pipe bone. In contrast the maxilla is in case of Cawood IV, V and VI classification mostly resorbed to an alveolar (jaw) crest shaped like a knife-edge with a concave cortical (outer) surface. In order to perform a successful vertical distraction histio-osteogenesis the appropriate attachment of the distractor to the resorbed alveolar (jaw) bone is essential. Considering the configuration and dimensions of the resorbed and atrophied mandible, the device of the present invention offers advantages above the distractors of the prior art.

The brackets of the device of the present invention enables the surgeon to position the distractor accurately without damaging the adjacent anatomical structures. Some devices of the prior art require bending or cutting the micro plates for adaptation in e.g. alveolar distraction of single diasthemas (gap resulting from the removal of a tooth). In the device of the present invention, the construction of the brackets is preferably rigid and manufactured out of one piece and is preferably not soldered, as is the case in many devices of the prior art.

In the device of the present invention, the brackets are positioned on the buccal (outside) surface (extra cortical) of the alveolar (jaw) bone and do not interfere with the neo-osteogenic (newly grown bone) site. However in the design of devices of the prior art, elements (for instance the microplates) are bent to and lie within the neo-osteogenic (newly grown bone) gap and interfere with the augmented bone. Therefore removal of the microplates after completion of distraction osteogenesis does not contribute to the stability of the newly distracted layer of bone and will lead to unpredictable results.

The device as proposed may be applied in the entire orofacial skeleton in order to lengthen and augment the jaws vertically and/or horizontally. The device of the present invention is preferably used for vertical osteogenesis through distraction. Preferably, the device of the present invention is used for distraction of a piece of bone from the jaw.

The device of the invention can be used for distraction of a single tooth defect. The device can also be used for distraction of a resorbed alveolar ridge. The osteotomies can be made and the microdistractors can be fixated to the mandible.

The device is preferably sterilized in an autoclave before use. Therefore the device is preferably autoclaved.

A further embodiment of the invention relates to a method of distracting two segments of bone using the device of the present invention. Preferably, the fixed bracket is connected to one segment of bone and the translating bracket is connected to the other segment of bone that is to be distracted away from the other segment of bone. Preferably, the distraction screw is inserted through the cylinder of the translating bracket and placed on (and preferably slotted into) the chamber of the fixed bracket. By turning the distraction screw, the two segments of bone are distracted.

Preferably, the segment of bone that is to be distracted is cut (osteomized) from the underlying jaw and the translating bracket is attached thereto. Preferably, the fixed bracket is attached to the underlying bone, for instance the jaw.

After placement of the device of the invention in the jaw of a patient, the device is preferably left for a period of 3 to 7 days. After this period, the translating bracket scan be moved up by 0.5 to 1.0 mm per day. Preferably, the distraction ranges from a 2 mm to an extreme of 5 mm, more preferably from 5 mm to 30 mm, most. preferably up to 20 mm.

Preferably, the entire distractor lies underneath the mucoperiosteal layer and will be activated one week after insertion, i.e. when healing of the tissues have commenced. The device is enwrapped in a soft tissue envelope (mucoperiost). This is a subperiosteal (submucosal) fixation. Hardly any friction is possible which prevent fraction of the device and the underlying pieces of bone.

The distracted bone may for instance enable placement of a dental implant.

It has to be understood that all dimensions mentioned in the application should preferably be interpreted as being about the size indicated. In this respect it is particularly preferred that the purpose of that aspect of the invention is taken into account.

EXAMPLES

Example 1

A device was manufactured with the following characteristics. The translating bracket comprises a cylinder, 2 perforations and 2 pins that match the perforations. The cylinder has an internal thread. The cylinder is located centrally (viewed in the frontal plane) of and anteriorly (viewed in the sagittal plane) to the translating bracket. The length of the cylinder runs perpendicularly to the plane of the bracket and perpendicularly to the plane of the distraction screw. The inner diameter of the cylinder is 2.0 mm, the thickness of the cylinder wall is 1.5 mm and the height of the cylinder is 3.0 mm.

The translating bracket comprises 2 perforations. The perforations are positioned in the horizontal to (viewed in a sagittal or transversal plane) the translating bracket, and are completely embedded in the bracket. The perforations are round, smooth and not internally threaded. The perforations match the diameter of the lateral pins and have a diameter of 0.9 mm. The perforations are located on either side of the cylinder. The thickness of the bracket around the perforation is 3.0 mm. The line of the perforations in the translating bracket is 90 degrees relative to the distraction screw, but might be placed at an angle of 45 degrees at an angle if more retention is required. The translating bracket has a width of smaller than 10 mm, a length of about 5 mm, and a thickness (including the cylinder) of about 5 mm.

The fixed bracket comprises one chamber with an aperture in the shape of a hollow cylinder. The diameter of the aperture in the chamber is 1.9 mm. The chamber has an aperture at the top, while the bottom of the aperture is solid and not perforated. The open top and the closed bottom of the aperture, together, allow the distraction screw to be inserted and turned freely. The bottom of the aperture is flat. The inner surface of the chamber is smooth and not threaded. The length of the cylindrically shaped aperture is 1.2 mm.

The length of the chamber is about 2.5 mm. The width of the chamber is about 4 mm. The chamber has a thickness of about 5 mm. The fixed bracket comprises 2 perforations on either side of the chamber. The perforations are positioned in the horizontal to (viewed in a sagittal or transversal plane) the fixed bracket and are completely embedded in the brackets. The perforations are round, smooth and not internally threaded. The perforations match the diameter of the lateral pins and have a diameter of about 0.9 mm.

The fixed bracket has the same dimensions as the translating bracket.

The device comprises one distraction screw with a head, a shaft and a tip. The length of the distraction screw is 20 mm. The head of the distraction screw has a groove. The groove covers the entire diameter of the head. The circumference of the head is hexagonally shaped. In order to enable the surgeon or patient to easily read the distance of distraction after having turned the distraction screw, the head of the distraction screw is marked on the surface between the center and the side of the screw. The mark may be a colored indentation in the screw.

The shaft of the distraction screw is threaded. The pitch of the thread is 0.25 mm The diameter of the shaft is 1.9 mm. The distraction screw is straight and does not have any extensions or indentations. The tip of the distraction screw is flat, smooth and polished tip. The lateral pins are threaded and are 4 mm in length with a diameter of 0.9 mm. The head of the lateral pin has a groove covering the entire diameter of the head. The pitch of the threads of the lateral pins is about 0.9 mm.

The device comprises a guiding rail continuously with the fixed bracket and made from one piece of Titanium with a smooth and polished surface. It is connected at the posterior (back) part of the fixed bracket and has a rounded top. The guiding rail has a length just short of the distraction screw. The guiding rail has a width of 3 mm. The guiding rail has a thickness of 1 mm.

The device does not have an interconnecting bar.

The distraction screw runs perpendicularly through the cylinder on the translating bracket. The screw turns in thread of the cylinder of the translating bracket. The distraction screw rests on the fixed bracket. By turning the distraction screw, the screw will push against the fixed bracket and move the translating bracket along the thread of the distraction screw.

The chamber of the fixed bracket is located entirely on one side of the cylinder of the translating bracket (when viewed in a sagittal or transversal plane). The cylinder of the translating bracket is located entirely outside of the chamber of the fixed bracket. The chamber of the fixed bracket and the rest of the fixed bracket are located on the same side of the translating bracket. Thus, the chamber of the fixed bracket does not extend to the other side of the cylinder of the translating bracket. The distraction screw rests on the bottom of the aperture in the chamber.

The distraction screw is inserted and turned freely in the aperture of the fixed bracket. The distraction screw rests on the bottom of the aperture. The distraction screw is inserted in the fixed bracket for about 1.5 mm.

The distraction screw does not have extensions inside in the aperture of the chamber of the fixed bracket. This allows the distraction screw to be removed from the fixed bracket through the aperture at the top and from the translating bracket (for instance to be exchanged for a shorter or preferably a longer screw). This allows the surgeon to replace the distraction screw, for instance with a longer distraction screw, during the process of distraction and without unscrewing the brackets from the underlying bone.

The device of the invention does not interfere with the site of neo-osteogenesis. The brackets do not have extensions that are directed perpendicularly to the distraction screw and perpendicularly to the brackets, at a level between the brackets and directed away from the distraction screw into the site of neo-osteogenesis. Also, the distraction screw is not present in the site of neo-osteogenesis which is away from the distraction screw viewed in a sagittal or transversal plane.

The lateral pins are located perpendicularly to the distraction screw and perpendicularly to the brackets (viewed in a sagittal or transversal plane). The lateral pins have a length of about 4 mm. The lateral pins do not interfere with the site of neo-osteogenesis and do not damage the surrounding anatomical structures. The guiding rail slides through the translating bracket.

The guiding rail is connected at the posterior (back) part of the bracket, posterior to the distraction screw and parallel to the distraction screw.

The device is activated by turning the distraction screw through the cylinder of the translating bracket and onto the fixed bracket onto or into the chamber, alongside the guiding rail, after fixation of the device by the lateral pins. The parts of the device are manufactured without using welding or soldered connections. Instead each part is manufactured out of one solid piece through casting.

We simulated the distraction process on a plexiglass model resembling the anatomical sizes of a human mandible. The device was applied in the mandible and maxillain order to distract the jaw vertically.

One piece of plastic of the model was distracted using the device. The translated bracket is connected to the osteotomized mandible piece to be distracted-and-that was cut from the underlying model. The fixed bracket was attached to the underlying mandible, the piece not to be distracted. The distraction screw is inserted through the cylinder of the translating bracket and placed on the chamber of the fixed bracket. By turning the distraction screw, the piece is distracted for 20 mm. The same was done for the maxilla, instead of the mandible.

The vertical upward movement of the translating bracket follows without difficulty and the fixated cranial (upper) part of the mandible can be lifted in a controlled fashion. The rigidity of the device is satisfying considering the absence of soft tissues on the model. It is not possible to bend or distort the device by digital tension force.

Example 2

A second device is manufactured. This device is the same as the first device, but without the guiding rail. Again the device distracted a piece of the model for 20 mm.

Example 3

A third device was manufactured. This device is half the size of the second device, apart from the length of the distraction screw, which was also 20 mm Again the device distracted a piece (part) of the model for 20 mm. When distracted at a length of 20 mm, a device with guiding rail is more stable and shows less torque. A device without guiding rail shows neither distortion nor bending at digital pressure in a mandibular model. While absent in the mandibular model, in the patient's mouth the periosteum and musculo-mucosal envelope would give additional rigidity and buccal tension to the device, likely to prevent the aforementioned slight transverse movement at maximum distraction length of 20 mm. The device was successfully tested in vitro. The design of the device takes into consideration the (specific) anatomical dimensions of the resorbed and atrophied mandible.

Example 4

A 29-year-old male with an anterior mandibular defect was treated by distraction histio-osteogenesis. Pre-operative planning was performed by measuring and assessing the clinical defect, plater models, an orthopantomogram and lateral skull X-ray. Prior to incision the outline of incisions and lines of osteotomy were drawn onto the mucosa. A device according to the invention as described in Example 1 was placed to assess its position in the (i) vertical (ii) transversal (iii) sagittal plane and (iv) to check its interference with the occlusal plane. Hereafter—using a microtome or microsaw—an osteotomy is performed. The following considerations to the osteotomy were given:

1. performance of a bicortical osteotomy
2. preferably at least 3–5 mm away from adjacent teeth
3. the vertical and horizontal lines of osteotomy are preferably connected using rounded angles
4. after completion of the osteotomy, the free segment could be mobilized from its underlying bone in 3 dimensions.

During the surgical procedure a microdistractor as described in this patent was used. Firstly the fixed bracket containing the guiding rail was fixed to the underlying alveolar bone in the midline of the mandibular defect. Fixation of the fixed bracket took place using 4 osteosynthetic pins of 7 mm in length. Hereafter the translating bracket was placed just above the line of osteotomy and in a vertical plane relative to the fixed bracket. The translating bracket was fixed with 4 osteosynthetic pins of 7 mm in length. Subsequently a distraction screw with a length of 20 mm was inserted through the cylinder of the translating bracket and resting on and slotting into chamber of the fixed bracket. During the surgical procedure the device was activated to approximately half of its length to simulate and anticipate the clinical distraction. The distraction screw was then returned by screwing back to its starting position to the point where the cranial and caudal osseous (bony) segments made contact. The vulnerae (wounds) were closed with an uninterrupted 4-0 Vicryl sutures. The head of the distractor was the only part allowed to protrude transmucosally. In order to protect the adjacent soft tissues of the oral cavity the head of the distraction screw was covered by a silastic tube. Post-operative the patient was given a chin bandage for support of the mental bandage.

Fixation of the device was performed by (i) placing the fixed bracket at least 3–5 mm away from the line of osteotomy (ii) placing the translating bracket at least 3–5 mm away from the line of osteotomy (iii) assuring that the distraction screw translates the segment in a satisfactory manner in 3 planes.

The device was activated to preview the transport until the moment that blanching of the soft tissues occurred. At this point the device was turned back until the point that both osseous segments made contact. The mucoperiosteum was closed in an uninterrupted fashion with 4-0 Vicryl sutures. Upon completion of the surgical procedure the head of the distraction screw was covered by a rubber or silastic hollow tube to protect the surrounding oral tissues. Activation commenced between 3–7 days post-operatively. The rate of activation was between 0.2–1.0 mm per day. After 2 weeks of activation, the device had created 10 mm of new alveolar bone, which was used for a dental implant.

The invention claimed is:

1. A vertical alveolar osteogenesis microdistractor device comprising: a translating bracket with a cylinder, a fixed bracket with a chamber with an aperture, a distraction screw, lateral pins for fixating the translating and fixed brackets to an underlying bone, and a guiding rail connecting the brackets and extending posterior and parallel to the distraction screw,
   wherein the aperture is smooth and not threaded,
   wherein the distraction screw is turned through the cylinder of the translating bracket and placed into the aperture of the chamber of the fixed bracket,
   the aperture of the chamber being adapted to allow the distraction screw to be inserted and turned freely in the chamber, the distraction screw being shaped such as to allow its removal from the fixed bracket through the aperture and from the translating bracket,
   wherein the chamber of the fixed bracket and the rest of the fixed bracket are entirely located at an anterior side of the translating bracket,
   wherein the distraction screw, the cylinder, and the chamber are located at the anterior side of a surface defined by the brackets and the guiding rail in the assembled state of the device, such that the distraction screw, the cylinder, and the chamber do not interfere with the osteogenesis site, and
   wherein the posterior orientation of said guiding rail relative to the distraction screw is such that the guiding rail is between the screw and a patient having the underlying bone.

2. The vertical alveolar osteogenesis microdistractor device of claim 1 wherein the chamber of the fixed bracket is a bottomed chamber.

3. The vertical alveolar osteogenesis microdistractor device of claim 1 wherein the device is smooth and without sharp edges.

4. The vertical alveolar osteogenesis microdistractor device of claim 1 wherein the guiding rail is integral with the fixed bracket and slidable into the translating bracket.

5. The vertical alveolar osteogenesis microdistractor device of claim 1 wherein the tip of the distraction screw is flat or spherical.

6. The vertical alveolar osteogenesis microdistractor device of claim 1 wherein the tip of the distraction screw is smooth and polished.

7. The vertical alveolar osteogenesis microdistractor device of claim 1 wherein the length of the aperture is larger than 0.8 mm and smaller than 15 mm.

8. A vertical alveolar osteogenesis microdistractor device comprising: a translating bracket with a cylinder, a fixed bracket with a chamber with an aperture, a distraction screw, lateral pins for fixating the translating and fixed brackets to the underlying bone, and a guiding rail connecting the brackets and extending posterior and parallel to the distraction screw,
   wherein the aperture is smooth and not threaded,
   wherein the distraction screw is turned through the cylinder of the translating bracket and placed into the aperture of the chamber of the fixed bracket,
   wherein the chamber of the fixed bracket and the rest of the fixed bracket are entirely located at a single side of the translating bracket,
   wherein the distraction screw, the cylinder, and the chamber are located at a single side of a surface defined by the brackets and the guiding rail in the assembled state of the device, such that the distraction screw, the cylinder, and the chamber do not interfere with the osteogenesis site, and
   wherein the posterior orientation of said guiding rail relative to the distraction screw is such that the guiding rail is between the screw and a patient having the underlying bone.

9. The vertical alveolar osteogenesis microdistractor device of claim 8 wherein the chamber of the fixed bracket is a bottomed chamber.

10. The vertical alveolar osteogenesis microdistractor device of claim 8 wherein the device is smooth and without sharp edges.

11. The vertical alveolar osteogenesis microdistractor device of claim 8 wherein the guiding rail is integral with the fixed bracket and slidable into the translating bracket.

12. The vertical alveolar osteogenesis microdistractor device of claim 8 wherein the tip of the distraction screw is flat or spherical.

13. The vertical alveolar osteogenesis microdistractor device of claim 8 wherein the tip of the distraction screw is smooth and polished.

14. The vertical alveolar osteogenesis microdistractor device of claim 8 wherein the length of the aperture is larger than 0.8 mm and smaller than 15 mm.

* * * * *